(12) United States Patent
Watt (10) Patent No.: US 12,419,884 B2
(45) Date of Patent: Sep. 23, 2025

(54) COMPOSITIONS AND METHODS FOR TREATING IRON OVERLOAD

(71) Applicant: BRIGHAM YOUNG UNIVERSITY, Provo, UT (US)

(72) Inventor: Richard K. Watt, Provo, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

(21) Appl. No.: 17/266,751

(22) PCT Filed: Aug. 6, 2019

(86) PCT No.: PCT/US2019/045314
§ 371 (c)(1),
(2) Date: Feb. 8, 2021

(87) PCT Pub. No.: WO2020/033412
PCT Pub. Date: Feb. 13, 2020

(65) Prior Publication Data
US 2021/0338657 A1  Nov. 4, 2021

Related U.S. Application Data

(60) Provisional application No. 62/715,188, filed on Aug. 6, 2018.

(51) Int. Cl.
| | | |
|---|---|---|
| *A61K 31/472* | (2006.01) | |
| *A61K 31/16* | (2006.01) | |
| *A61K 31/4196* | (2006.01) | |
| *A61K 31/427* | (2006.01) | |
| *A61K 31/4412* | (2006.01) | |
| *A61P 39/04* | (2006.01) | |

(52) U.S. Cl.
CPC ............ *A61K 31/472* (2013.01); *A61K 31/16* (2013.01); *A61K 31/4196* (2013.01); *A61K 31/427* (2013.01); *A61K 31/4412* (2013.01); *A61P 39/04* (2018.01)

(58) Field of Classification Search
CPC .................................................. A61K 31/472
See application file for complete search history.

(56) References Cited

U.S. PATENT DOCUMENTS

2008/0187510 A1   8/2008  Camenisch et al.
2016/0324831 A1   11/2016 Malhotra et al.

FOREIGN PATENT DOCUMENTS

WO         98/04290 A2    2/1998
WO  WO-2017147078 A1 *  8/2017  ............ A61K 31/427

OTHER PUBLICATIONS

Andrew Gross, "Discovery of an Allosteric Site on Furin, contributing to Potent Inhibition: a Promising Therapeutic for the Anemia of Chronic Inflammation", Jul. 1, 2014, These and Dissertations, BYU ScholarsArchive (Year: 2014).*
Andrew Gross, "Discovery of an Allosteric Site on Furin, contributing to Potent Inhibition: a Promising Therapeutic for the Anemia of Chronic Inflammation", Oct. 2016, These and Dissertations, BYU ScholarsArchive (Year: 2016).*
"#8 Reticuloendothelial system and function of the spleen", Physiology435, Jan. 28, 2017 (Year: 2017).*
"Treating Thalassemia: Chelation -Desferal", Northern California Comprehensive Thalassemia Center, Jun. 15, 2006 (Year: 2006).*
"Beta Thalassemia", Johns Hopkins Medicine, Sep. 2, 2016 (Year: 2016).*
Musallam and Taher, "Mechanism of Renal Disease in Beta-Thalassemia", Science in Renal Medicine, pp. 1299-1302, Aug. 1, 2012 (Year: 2012).*
Origa et al., "Treatment of Hepatitis C virus infection with direct-acting antiviral drugs is safe and effect in patients with hemoglobinopathies", American Journal of Hematology, vol. 92, Issue 12, Nov. 7, 2017 (Year: 2017).*
Baas et al., "The reticuloendothelial system. An overview of function, pathology and recent methods of measurement", Z Gastroenterol. Feb. 1994 (Year: 1994).*
Coyne DW, "Iron Overload in Dialysis Patients: Rust or Bust?", Kidney Int Rep., Sep. 1, 2017 (Year: 2017).*
"Norvir (ritonavir) Label", FDA, Jun. 2017 (Year: 2017).*
International Search Report for PCT/US2019/045314, dated Oct. 21, 2019.
Moreira, Ana C., et al. Ferritin: an Inflammatory Player Keeping Iron at the Core of Pathogen-Host Interactions. Microorganisms(2020), 8, 589. https://doi.org/10.3390/microorganisms8040589.
Shan, Ying, et al. Association of Hepatitis C Virus Infection with Serum Iron Status: Analysis of Data from the Third National Health and Nutrition Examination Survey. Clinical Infectious Diseases. vol. 40, No. 6 (Mar. 15, 2005), pp. 834-841.
Lee, Yen-Chien, et al. Thalassemia Intermedia: Chelator or Not? Int. J. Mol. Sci. 2022, 23, 10189. https://doi.org/10.3390/ijms231710189.
Au, Tsz Yuen, et al. Is the Role of Hepcidin and Erythroferrone in the Pathogenesis of Beta Thalassemia the Key to Developing Novel Treatment Strategies? Thalass. Rep. 2022, 12, 123-134. https://doi.org/10.3390/thalassrep12030017.

(Continued)

*Primary Examiner* — Andrew D Kosar
*Assistant Examiner* — Gillian A Hutter
(74) *Attorney, Agent, or Firm* — Ryan L. Marshall; Barnes &Thornburg LLP (57) ABSTRACT

The present disclosure relates to compositions and methods for treating iron overload. In particular, the methods for treating iron overload include administering to a patient an HIV protease inhibitor and an iron chelator. Iron overload may occur in patients diagnosed with anemia from inflammation or from chronic disease including hemochromatosis, sickle cell disease, thalassemia, sideroblastic anemia, an enzyme deficiency, pre-operative anemia, a cardiovascular disease, atransferrinemia, or aceruloplasminemia.

11 Claims, 9 Drawing Sheets

(56) References Cited

OTHER PUBLICATIONS

Eshagh Hossaini, S.K., et al. Association between serum levels of hepcidin and ferritin in patients with thalassemia major and intermedia, the role of iron chelator. J Hematopathol 12, 143-147 (2019). https://doi.org/10.1007/s12308-019-00363-x.
Pasricha, Sant-Rayn, et al. Transfusion suppresses erythropoiesis and increases hepcidin in adult patients with β-thalassemia major: a longitudinal study. Blood 2013; 122 (1): 124-133. doi: https://doi.org/10.1182/blood-2012-12-471441.
Susanah, Susi, et al. Iron Status in Newly Diagnosed β-Thalassemia Major: High Rate of Iron Status due to Erythropoiesis Drive. BioMed Research International, vol. 2021, Article ID 5560319, 7 pages, 2021. https://doi.org/10.1155/2021/5560319.
Parrow, Nermi L., et al. Lobe specificity of iron binding to transferrin modulates murine erythropoiesis and iron homeostasis. Blood. Oct. 24, 2019;134(17):1373-1384. doi: 10.1182/blood.2018893099. PMID: 31434707; PMCID: PMC6839954.

\* cited by examiner

COMPOSITIONS AND METHODS FOR TREATING IRON OVERLOAD

CROSS-REFERENCE TO RELATED APPLICATIONS

This application is a 371 national phase of PCT/US2019/012869, filed Jan. 9, 2019, which claims the benefit of U.S. Provisional Patent Application No. 62/715,188, filed Aug. 6, 2018, the entire contents of each of which are hereby incorporated herein by reference.

TECHNICAL FIELD

The invention described herein relates to compositions and methods for treating iron overload. In particular, the methods for treating iron overload include administering to a patient an HIV protease inhibitor and an iron chelator.

BACKGROUND INFORMATION

There are many iron disorders that result in excess iron being sequestered in the reticuloendothelial system (RES) that is made up of the liver, spleen and macrophages that recycle senescent red blood cells. For example, thalassemia patients frequently require blood transfusions to have sufficient healthy hemoglobin to carry oxygen due to improper folding of the patient's hemoglobin subunits. When the red blood cells from the transfusion die and are recycled, the iron delivered by the transfusion is eventually deposited in the RES. This results in liver and spleen iron overload. Hemochromatosis is a genetic condition where the ability to regulate iron absorption is lost due to mutations and results in RES iron overload. Myelofibrosis is a blood cancer that often requires blood transfusions and results in iron overload from the iron given in the transfusion. Myelofibrosis patients are also trying to produce their own red blood cells, so iron absorption genes are also upregulated facilitating additional iron sequestration in the RES. Any inflammatory condition that requires transfusions can lead to iron overload in the RES.

Dialysis patients and inflammatory bowel disorder patients are anemic and are treated with intravenous (IV) iron supplements. Remarkably, RES iron overload occurs in these patients. The IV iron treatments are given to supplement iron depletion in the bone marrow. This is done in an attempt to stimulate hemoglobin synthesis for red blood cell production. Unfortunately, these conditions are accompanied by chronic inflammation and the majority of the IV iron supplement is not delivered to the bone marrow but absorbed by the RES and in some cases the heart. Elevated iron is dangerous because elevated iron can catalyze oxidative stress and damage to these organs.

Figure 1:
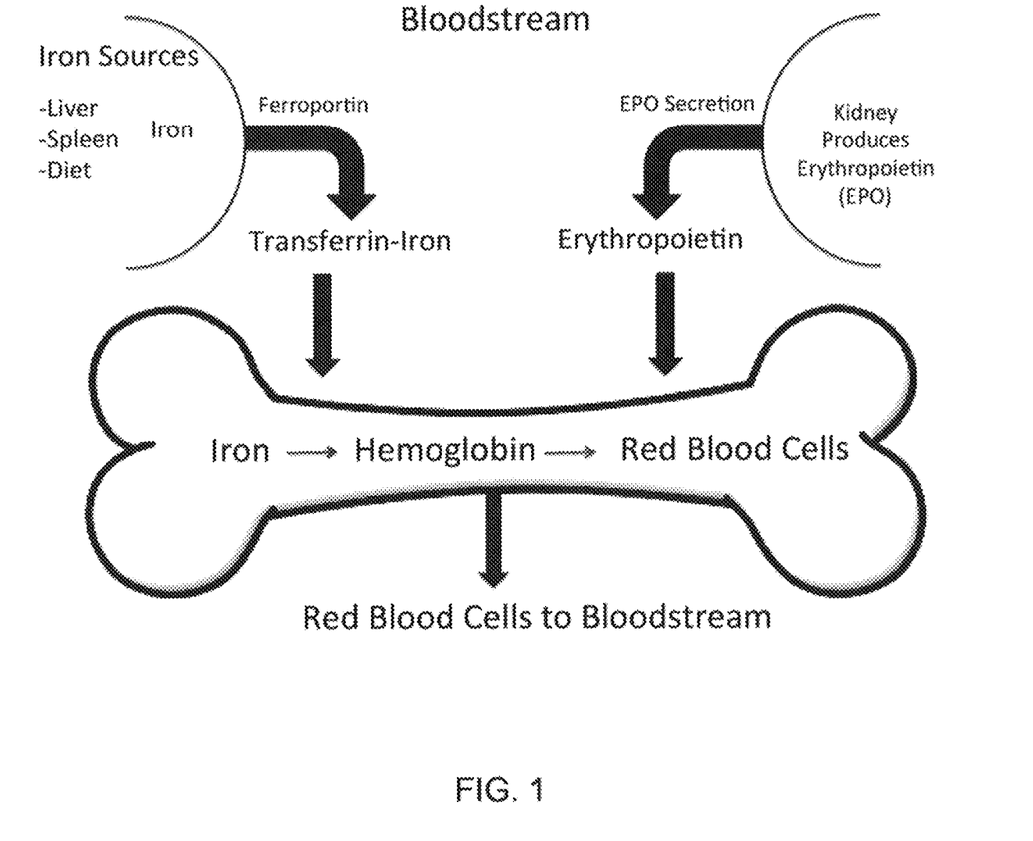
FIG. 1 shows the normal process of iron release form the liver and spleen and how iron is absorbed from the intestines and delivered to the proper locations such as the bone marrow for red blood cell synthesis.
Figure 2:
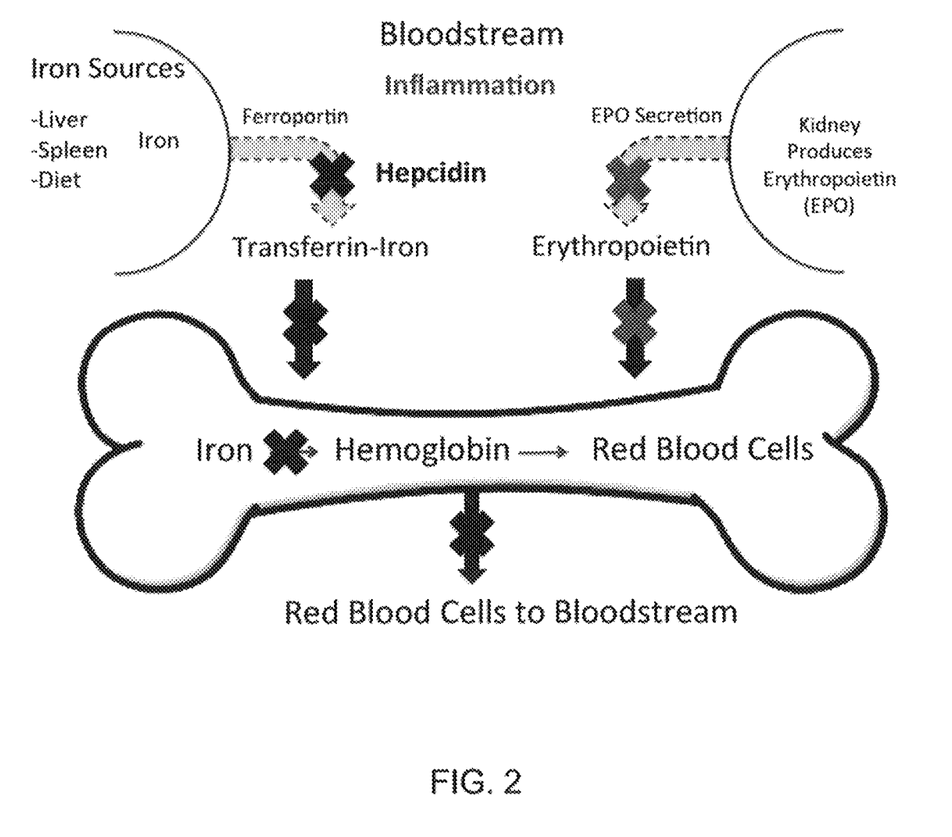
FIG. 2 shows a conceptual schematic of the effects of inflammation. Inflammation produces hepcidin that binds to ferroportin and causes its degradation. This stops iron delivery to the bone marrow. Inflammation also blocks EPO production and secretion from the kidneys. Combined these effects decrease red blood cell synthesis resulting in anemia.

Since humans do not have an iron excretion mechanism, excess iron from blood transfusions or from IV iron leads to iron overload in the RES. In addition, some of the conditions listed above are accompanied by inflammation which upregulates hepcidin. Hepcidin is an iron regulatory hormone that disrupts normal iron distribution in the body. FIG. 1 shows the normal process of iron release from the liver and spleen and how iron is absorbed from the intestines and delivered to the proper locations such as the bone marrow for red blood cell synthesis. Ferroportin is critical for normal iron absorption from the diet and iron redistribution from the liver and spleen so that iron can be recycled back to the bone marrow for red blood cell synthesis. FIG. 2 shows how hepcidin causes the degradation of ferroportin and disrupts normal iron processing. This results in iron being trapped in the RES and prevents normal iron absorption when iron is required by the body.

For conditions that result in iron overload caused by genetic hemochromatosis or from excess iron acquired by blood transfusions, conventional treatment includes administering iron chelators to alleviate the iron overload in the RES and facilitate iron secretion from the body. Early hydrophilic chelators successfully bound iron in the serum, but these chelators do not diffuse across cell membranes to enter iron overloaded tissues to remove iron trapped in the RES. New hydrophilic chelator treatments have been developed where the chelator can diffuse into cells and access iron in the tissues followed by diffusion out of the cell to the bloodstream where the chelator-iron complex can be secreted by the kidneys. Unfortunately, both classes of iron chelators deplete serum and/or cellular iron that is essential for iron-dependent enzymes. Depleting these iron pools causes side effects as these iron pools are sources of iron for other proteins and enzymes that require iron for proper function. Therefore, iron chelators produce dangerous side effects.

New treatments for iron overload are needed to address the shortcomings of current clinical practice.

BRIEF SUMMARY

A method of treating iron overload in a patient is provided. The method may include administering to the patient a therapeutically effective amount of at least one HIV protease inhibitor and an iron chelator.

In some aspects, the HIV protease inhibitor may be selected from: amprenavir, atazanavir, darunavir, fosamprenavir, indinavir, lopinavir, nelfinavir, ritonavir, saquinavir, tipranavir, and any combination thereof.

In some aspects, the HIV protease inhibitor may be selected from: nelfinavir, darunavir, ritonavir, tipranavir, and any combination thereof.

In some aspects, the HIV protease inhibitor may be selected from: nelfinavir, darunavir, ritonavir, and any combination thereof.

In some aspects, at least two HIV protease inhibitors may be administered to the patient.

In some aspects, the at least two HIV protease inhibitors may be nelfinavir and ritonavir.

In some aspects, the iron chelator may be selected from: desferal, deferasirox, deferiprone, and any combination thereof.

In some aspects, the patient has chronic inflammation. In some aspects, the patient has anemia from chronic disease. In some aspect, the patient may be diagnosed with any one or more of: hemochromatosis, sickle cell disease, thalassemia, sideroblastic anemia, an enzyme deficiency, preoperative anemia, a cardiovascular disease, atransferrinemia, or aceruloplasminemia.

In some aspects, the patient may be undergoing dialysis.

In some aspects, the patient may be diagnosed with inflammatory bowel disease (IBD).

In some aspects, the administering to the patient the therapeutically effective amount of the HIV protease inhibitor and the iron chelator may lower serum hepcidin concentration.

In some aspects, the administering to the patient the therapeutically effective amount of the HIV protease inhibitor and the iron chelator may lower iron concentration in reticuloendothelial system.

In some aspects, the patient may be diagnosed with myelofibrosis.

In some aspects, the iron concentration in the spleen may be reduced.

In some aspects, the HIV protease inhibitor and the iron chelator may be provided as a pharmaceutical composition for oral administration.

A pharmaceutical combination comprising an HIV protease inhibitor and an iron chelator is also provided.

In some aspects, the pharmaceutical combination may include a HIV protease inhibitor that is selected from: amprenavir, atazanavir, darunavir, fosamprenavir, indinavir, lopinavir, nelfinavir, ritonavir, saquinavir, tipranavir, and any combination thereof.

In some aspects, the pharmaceutical combination may include an iron chelator that is selected from: desferal, deferasirox, deferiprone, and any combination thereof.

In some aspects, the pharmaceutical combination may include at least two HIV protease inhibitors, wherein the HIV protease inhibitors are nelfinavir and ritonavir.

DETAILED DESCRIPTION

The following description defines in more detail the embodiments of the invention described herein. The following embodiments are not meant to limit the invention or narrow the scope thereof, as it will be readily apparent to one of ordinary skill in the art that suitable modifications and adaptations may be made without departing from the scope of the invention, embodiments, or specific aspects described herein. All patents and publications cited herein are incorporated by reference herein in their entirety.

For purposes of interpreting this specification, the following terms and definitions will apply and whenever appropriate, terms used in the singular will also include the plural and vice versa. In the event that any definition set forth below conflicts with any document incorporated herein by reference, the definition set forth below shall control.

The term "patient" refers to any subject including mammals and humans. The patient may have a disease or suspected of having a disease and as such is being treated with a drug. In some instances, the patient is a mammal, such as a dog, chicken, cat, horse, or primate. In some instances, the term "patient," as used herein, refers to a human (e. g., a man, a woman, or a child). In some instances, the term "patient," as used herein, refers to laboratory animal of an animal model study. The patient or subject may be of any age, sex, or combination thereof.

The terms "active ingredient," "active pharmaceutical ingredient," "bioactive agent," or "therapeutic agent" as used herein refer to a pharmaceutical agent, active ingredient, compound, substance or drug, compositions, or mixtures thereof, that provide a pharmacological, often beneficial, effect. The active ingredient may be any pharmaceutically acceptable salt, hydrate, crystalline form or polymorph thereof.

The term "formulation" or "composition" as used herein refers to the active ingredient or drug in combination with pharmaceutically acceptable excipients.

The terms "dosage" or "dose" as used herein denote any form of the active ingredient formulation that contains an amount sufficient to produce a therapeutic effect with a single administration.

The term "treating" refers to administering a therapy in an amount, manner, or mode effective to improve a condition, symptom, or parameter associated with a disorder. In some embodiments, treating refers to the amelioration of pain stemming from arthritis (e. g., osteoarthritis) or a musculoskeletal pain. In some embodiments, treating refers to the reversal of a disease process, such as arthritis (e. g., osteoarthritis) and permanent healing.

A method of treating iron overload in a patient is provided. The method may include administering to the patient a therapeutically effective amount of at least one HIV protease inhibitor and an iron chelator.

The HIV protease inhibitor may be amprenavir ((3S)-oxolan-3-yl N-[(2S,3R)-3-hydroxy-4-[N-(2-methylpropyl)(4-aminobenzene)sulfonamido]-1-phenylbutan-2-yl]carbamate), atazanavir (methyl N-[(1S)-1-{[(2S,3S)-3-hydroxy-4-[(2S)-2-[(methoxycarbonyl)amino]-3,3-dimethyl-N'-{[4-(pyridin-2-yl)phenyl]methyl}butanehydrazido]-1-phenylbutan-2-yl]carbamoyl}-2,2-dimethylpropyl]carbamate), darunavir ([(1R,5S,6R)-2,8-dioxabicyclo[3.3.0]oct-6-yl] N-[(2S,3R)-4-[(4-aminophenyl)sulfonyl-(2-methylpropyl) amino]-3-hydroxy-1-phenyl-butan-2-yl]carbamate), fosamprenavir[(2R,3S)-1-[N-(2-methylpropyl)(4-aminobenzenesulfonamido]-3-({[(3S)-oxolan-3-yloxy]carbonyl}amino)-4-phenylbutan-2-yl]oxyphosphonic acid, indinavir ((2S)-1-[(2S,4R)-4-benzyl-2-hydroxy-4-{[(1S,2R)-2-hydroxy-2,3-dihydro-1Hinden-1-yl]carbamoyl}butyl]-N-tert-butyl-4-(pyridin-3-ylmethyl)piperazine-2-carboxamide), lopinavir ((2S)—N-[(2S,4S,5S)-5-[2-(2,6-dimethylphenoxy)acetamido]-4-hydroxy-1,6-diphenylhexan-2-yl]-3-methyl-2-(2-oxo-1,3-diazinan-1-yl)butanamide), nelfinavir ((3S,4aS, 8aS)—N-tert-butyl-2-[(2R,3R)-2-hydroxy-3-[(3-hydroxy-2-methylphenyl)formamido]-4-(phenylsulfanyl)butyl]-decahydroisoquinoline-3-carboxamide), ritonavir[(1,3-thiazol-5-ylmethylN-R2S,3S,5S)-3-hydroxy-5-[(2S)-3-methyl-2-{[methyl({[2-(propan-2-yl)-1,3-thiazol-yl]methyl}) carbamoyl]amino}butan-amido]-1,6-diphenylhexan-2-yl] carbamate), saquinavir ((2S)—N-[(2S,3R)-4-[(3S)-3-(tert-butylcarbamoyl)-decahydroisoquinolin-2-yl]-3-hydroxy-1-phenylbutan-2-yl]-2-(quinolin-2-yl-formamido)butanediamide), tipranavir (N-{3-[(1R)-1-[(2R)-6-hydroxy-4-oxo-2-(2-phenylethyl)-2-propyl-3,4-dihydro-2H-pyran-5-yl]propyl]phenyl}-5-(trifluoromethyl)pyridine-2-sulfonamide), and combinations thereof.

In some aspects, the HIV protease inhibitor may be nelfinavir, darunavir, ritonavir, tipranavir, or any combination thereof. In some aspects, the HIV protease inhibitor may be nelfinavir, darunavir, ritonavir, or any combination thereof. In some aspects, HIV protease inhibitor may be amprenavir. In some aspects, HIV protease inhibitor may be atazanavir. In some aspects, HIV protease inhibitor may be darunavir. In some aspects, HIV protease inhibitor may be fosamprenavir. In some aspects, HIV protease inhibitor may be indinavir. In some aspects, HIV protease inhibitor may be lopinavir. In some aspects, HIV protease inhibitor may be nelfinavir. In some aspects, HIV protease inhibitor may be ritonavir. In some aspects, HIV protease inhibitor may be saquinavir. In some aspects, HIV protease inhibitor may be tipranavir.

In some aspects, the HIV protease inhibitor may be a prodrug of any of the aforementioned HIV protease inhibitors. For example, the prodrug may be FosAmprenavir.

In some aspects, at least two HIV protease inhibitors may be administered to the patient. In some aspects, the at least two HIV protease inhibitors may be nelfinavir and ritonavir.

In some aspects, the method may include administration of a pharmaceutical composition. In some aspects, the pharmaceutical composition may include at least one HIV protease inhibitor and an iron chelator.

In some aspects, the iron chelator may be any suitable iron chelator. Examples of iron chelators include, but are not limited to, desferal, deferasirox, and deferiprone.

In some aspects, administering to the subject an HIV protease inhibitor may inhibit furin activity. In some aspects, inhibiting furin activity may inhibit the formation of hepcidin from the precursor prohepcidin. In some aspects, inhibition of hepcidin may increase the activity of ferroportin iron transport, resulting in increased concentration of iron into the bloodstream.

In some aspects, the pharmaceutical composition may include the one or more HIV protease inhibitors in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 mg, or an amount within a range defined by any two of the aforementioned values.

In some aspects, the pharmaceutical composition may include the iron chelators in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 mg, or an amount within a range defined by any two of the aforementioned values.

In some aspects, the one or more HIV protease inhibitors and iron chelator may be administered twice daily, once daily, once weekly, or once monthly, or a value within a range defined by any two of the aforementioned values.

Routes of administering the HIV protease inhibitor and iron chelator include, but are not limited to, intravenous, intramuscular, subcutaneous, intraarticular, oral, topical, intradermal, transdermal, subdermal, parenteral, rectal, spinal, or epidermal administration. In some aspects, the HIV protease inhibitor and iron chelator may be administered orally. In some aspects, the HIV protease inhibitor and iron chelator may be administered in combination with a pharmaceutically acceptable carrier suited for the mode of administration.

In some aspects, the compositions include a pharmaceutically acceptable carrier. "Pharmaceutically acceptable" carriers are ones which are nontoxic to the cell or subject being exposed thereto at the dosages and concentrations employed. "Pharmaceutically acceptable" carriers can be, but are not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also include one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counter ions such as sodium, and nonionic surfactants such as Tween™, polyethylene glycol (PEG), and Pluronics™. Auxiliary, stabilizer, emulsifier, lubricant, binder, pH adjustor controller, isotonic agent and other conventional additives may also be added to the carriers. The pharmaceutically acceptable or appropriate carrier may include other compounds known to be beneficial to an impaired situation of the GI tract, (e. g., antioxidants, such as vitamin C, vitamin E, selenium or zinc); or a food composition.

Multiple medical conditions exist where iron is trapped in the RES. The presence of hepcidin and ferroportin significantly influence iron sequestration or release from the RES.

Dialysis and inflammatory bowel disorders (IBD) are conditions where chronic inflammation is present and hepcidin is elevated. These conditions result in anemia of inflammation and are used as examples of the entire class of anemia of chronic inflammation disorders caused by elevated hepcidin. Current treatments include IV iron supplements and erythropoietin stimulating agents (ESAs). The use of IV iron has the goal of loading the bone marrow with iron but results show that only ~5% of the iron is bound by transferrin and ultimately delivered to the bone marrow and the rest of the IV iron is sequestered in the RES because of elevated hepcidin. Treatments with HIV PIs will lower serum hepcidin levels and prevent ferroportin from being degraded. This ferroportin stabilization treatment will stimulate release of IV iron from the RES and allow its export into the bloodstream, binding to transferrin and ultimately the delivery of iron to the bone marrow for heme synthesis in red blood cells.

Myelofibrosis is a blood cancer disorder where fibrosis in the bone marrow disrupts normal red blood cell synthesis. Myelofibrosis is accompanied by chronic inflammation and elevated hepcidin levels and splenomegaly with high iron levels in the spleen. Some of these patients are treated with IV iron to try to stimulate red blood cell synthesis. Additionally, the anemia can become so severe that blood transfusions are required. In both of these situations iron will be sequestered in the RES because of the elevated hepcidin levels and diminished ferroportin levels.

Treatment with HIV protease inhibitors will lower hepcidin levels. The lower hepcidin levels will allow for ferroportin stabilization and iron release from the spleen and other components of the RES. Iron will be more efficiently delivered to the bone marrow facilitating any red blood cell synthesis that is still available in the bone marrow.

A variety of thalassemia diseases exist. Hemoglobin is a tetramer comprised of two alpha and two beta subunits. The disease known as thalassemia occurs because alpha or beta chains of hemoglobin are defective due to mutations or because the ratio of alpha to beta chain synthesis is imbalanced and incorrect ratios of alpha and beta subunits are present. If the ratio is incorrect, excess alpha subunits or excess beta subunits try to assemble as all alpha or all beta subunits and these assemblies do not function properly for normal oxygen transport. In fact, these assemblies create oxygen radicals that cause oxidative stress and inflammation. Without properly folded and assembled hemoglobin, oxygen transport is severely diminished in these patients. Since the body senses oxygen levels from oxygen transport from hemoglobin in red blood cells, and recognizes hemoglobin is not transporting oxygen, the body tries to absorb more iron and increases red blood cell synthesis. This natural response can further separate the proper balance between alpha and beta subunits.

Some thalassemia conditions have low or normal hepcidin levels, but some have elevated hepcidin levels depending on the class of thalassemia and also the stage of the condition and treatments used and the accompanying inflammation. The increased hepcidin comes from inflammation and oxidative stress, and the resulting iron overload in the liver will initiate signals to upregulate hepcidin using BMP-6 when elevated iron is sensed in the liver.

In some aspects, the patient may be diagnosed with any one or more of: hemochromatosis, sickle cell disease, thalassemia, sideroblastic anemia, an enzyme deficiency, preoperative anemia, a cardiovascular disease, atransferrinemia, or aceruloplasminemia. In some aspects, the patient may be diagnosed with inflammatory bowel disease (IBD).

In some aspects, treatment may include administering an HIV protease inhibitor before administering the iron chelator.

Also, the method may include taking a blood sample from the patient to determine the levels of iron in the RES. The iron levels in the RES can be estimated by a series of tests that include serum ferritin, transferrin, transferrin saturation (TSAT) and hepcidin. When markers of iron overload in the RES are observed, the patients can be treated with HIV protease inhibitors to lower hepcidin and stabilize ferroportin and allow iron to be exported from the RES to minimize iron overload and oxidative stress from the liver and spleen. Timing of these treatments could be based on serum hepcidin levels, serum ferritin levels, transferrin saturation levels (TSAT), BMP-6 levels, and C-reactive protein in thalassemia patients. Serum ferritin is a good indicator of total body stores if inflammation is low and the inflammatory status of the individual can be measured by C-reactive protein. TSAT shows the levels of iron being transported by transferrin and if low, the measurement would indicate how much iron is being released from the liver for delivery to the bone marrow. BMP-6 is a marker of elevated liver iron and turns on the synthesis of hepcidin. A combined evaluation of BMP-6 and hepcidin in relation to serum ferritin and TSAT could be an effective way to manage when a thalassemia patient would require ferroportin stabilization treatment to release excess sequestered iron in the RES.

An alternate method to evaluate iron overload is to collect monocytes from blood as a representative cell for the RES. The evaluation of the total iron content and the internal labile iron pool of monocytes has been proposed to be a good representation of the iron load in the liver and spleen. Additionally, the ferroportin content on the surface of these cells can be correlated to the ferroportin present on the surface of the liver and spleen. Such tests can be used as a second method to estimate of the total iron load in the RES. Similar studies can be performed in macrophages to evaluate total iron and the labile iron pool. In addition, macrophages can be evaluated for the M1 to M2 macrophage transition associated with inflammation that can be caused by iron overload. The use of HIV protease inhibitors to lower hepcidin and stabilize ferroportin, macrophages can lower their internal iron and by decreasing the iron stress in the macrophage population, the overall inflammatory state of the body might be influenced in a positive manner.

It is anticipated that these periodic ferroportin stabilization treatments to release iron from the RES using the HIV protease inhibitors can be periodically coordinated with the hepcidin analogs treatments to maximize the hemoglobin synthesis and minimize iron overload.

Hemochromatosis is represented by a series of genetic disorders where regulation of iron absorption and sequestration has lost regulation and tissues are overloaded with iron. Iron chelation treatment as described above using hydrophilic or hydrophobic iron chelators is the current state of the art treatment. As indicated above, hydrophobic chelators cannot directly access iron in tissue but clear the bloodstream of iron. The hydrophilic chelators can enter the cells and facilitate iron egress from cells, but the affinity of some of these chelators is lower than transferrin and some of the iron is transferred back to transferrin and is subsequently delivered back to the overloaded tissues. Again, depletion of normal iron pools in the serum and cytosol caused dangerous side effects for chelator treated individuals.

In some aspects, the patient may be undergoing dialysis.

In some aspects, the administering to the patient the therapeutically effective amount of the HIV protease inhibitor and the iron chelator may lower serum hepcidin concentration.

In some aspects, the administering to the patient the therapeutically effective amount of the HIV protease inhibitor and the iron chelator may lower iron concentration in reticuloendothelial system.

In some aspects, the patient may be diagnosed with myelofibrosis.

In some aspects, the iron concentration in the spleen may be reduced.

In some aspects, the HIV protease inhibitor and the iron chelator may be provided as a pharmaceutical composition for oral administration.

A pharmaceutical combination comprising an HIV protease inhibitor and an iron chelator is also provided.

In some aspects, the pharmaceutical combination may include at least two HIV protease inhibitors, wherein the HIV protease inhibitors are nelfinavir and ritonavir.

Without being bound by any particular theory, it is believed that the compositions and methods disclosed herein can treat any condition or disease where a precursor protein called a proprotein similar to prohepcidin can be cut by furin to remove the 'Pro" domain and become activated. The new discovery can be applied to treating conditions or diseases where a protein or enzyme or cytokine that is activated by furin has a negative effect on the body once this activation has occurred. Inhibition of furin will block the proprotein conversion into the active protein, enzyme or cytokine and can be used as a treatment for that condition or disease.

Below we list examples of some proproteins and some related diseases related to the proproteins. Pro matrix metallo proteinase enzymes (ProMMPs) that are converted into active matrix metallo proteinase enzymes (MMPs). Examples of conditions relating to MMPs include periodontitis, cancer metastasis, organ fibrosis, and wounds that will not heal. MMPs that require furin for processing are known to include the following MMPs: MMP1, MMP2, MMP 3, shedding of MMP5, MMP 7, MMP8, MMP9, MMP10, MMP11, MMP12, MMP13, MMP14, MMP 15, MMP16, MMP17, MMP19, MMP20, MMP21, MMP23, MMP24, MMP25, MMP 26, MMP27, and MMP 28.

Furin is known to be upregulated by inflammation and the elevated concentrations of furin can contribute to the faster processing of substrates. Conditions where furin is upregulated by mutation or by other means can also be treated with HIV protease inhibitors.

Furin processes inactive precursor Procytokines to active cytokines. Any inflammatory process where inhibition of cytokine activation can be used to lower the inflammatory state of an individual for a beneficial treatment can be performed by treating the individual with HIV Protease inhibitors. Cytokines activated by furin include: Transforming Growth Factor-Beta (TGF-β), Tumor Necrosis Factor alpha (TNF-α), Bone morphogenic proteins, and Interleukins.

Furin processes many other proteins and enzymes, viruses, bacterial toxins and hormones and include: Human Insulin proreceptor, Low Density Lipoprotein receptor-related protein, Heparin-binding region of extracellular superoxide dismutase, Secreted semaphorins, Beta-secretase, Processing of proendothelin-1, Colon Carcinoma, processing of Influenza virus hemagglutinin, Intestinal prolactase, processing of viral glycoproteins (gp160), Processing of Ebola Virus, Processing of tick-borne encephalitis, Human parainfluenza, Hepatitis B virus type 3, Human cytomegalovirus glycoprotein B, Murine Coronavirus spike protein, Baculovirus, Semliki Forest virus, Ebola Virus glycoprotein, Anthrax toxin processing, *Clostridium parvum* glycoprotein gp40/15. HIV protease inhibitors have the potential to treat any of these conditions based on the fact that Furin processes these into active forms and these inhibitors block this action.

EXAMPLES

Example 1

Figure 3:
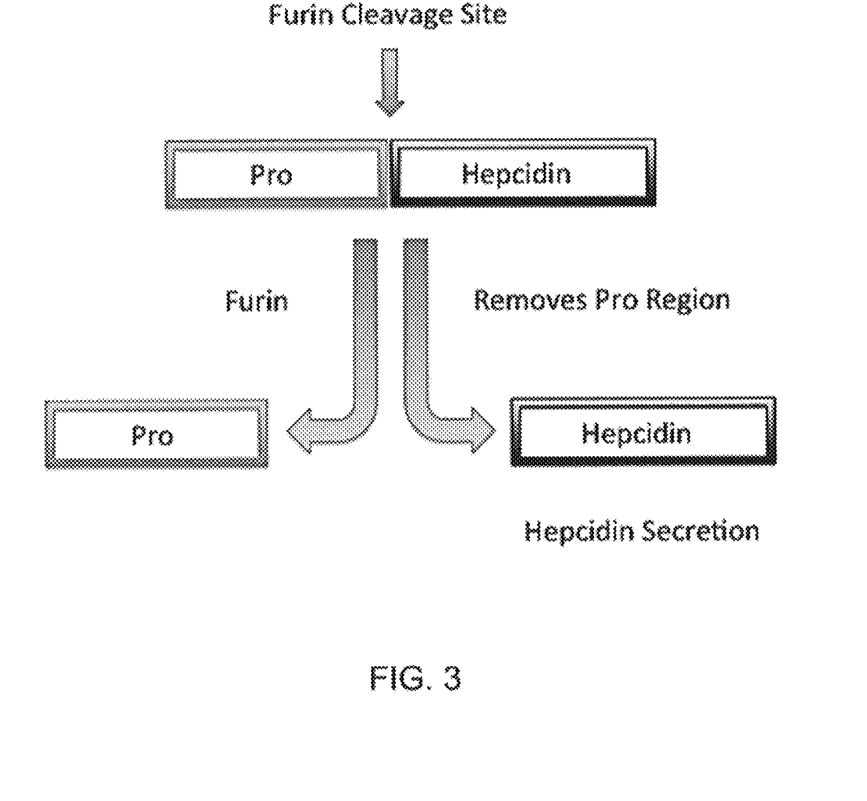
FIG. 3 shows furin cleavage of inactive prohepcidin into active hepcidin.

Some of the HIV protease inhibitors have an off-target inhibition of the protease furin. This is important because hepcidin is synthesized as an inactive precursor called prohepcidin. Furin cuts the inactive prohepcidin in to the active hepcidin (see FIG. 3).

Proof of concept for this hypothesis was shown through computer docking studies that identified two binding sites for these drugs. A catalytic site and an allosteric site were identified. Enzyme assays with purified furin showed these drugs inhibit furin and in combination, a catalytic site inhibitor and an allosteric site inhibitor inhibited furin synergistically. Table 1 lists the drugs and identifies them as catalytic site inhibitors or allosteric site inhibitors.

TABLE 1

Affinity of Drugs Binding Furin

| Drug Name | Catalytic Site ΔG kcal/mol | Allosteric Site ΔG kcal/mol |
| --- | --- | --- |
| Dec-RVKR-CMK | −11.07 | −9.25 |
| Amprenavir | — | −7.81 |
| Atazanvir | — | −8.82 |
| Darunavir | — | −8.18 |
| Lopinavir | — | −7.6 |
| Nelfinavir | −8.24 | −8.82 |
| Ritonavir | — | −8.57 |
| Tipranavir | — | −8.58 |

Example 2

Figure 4:
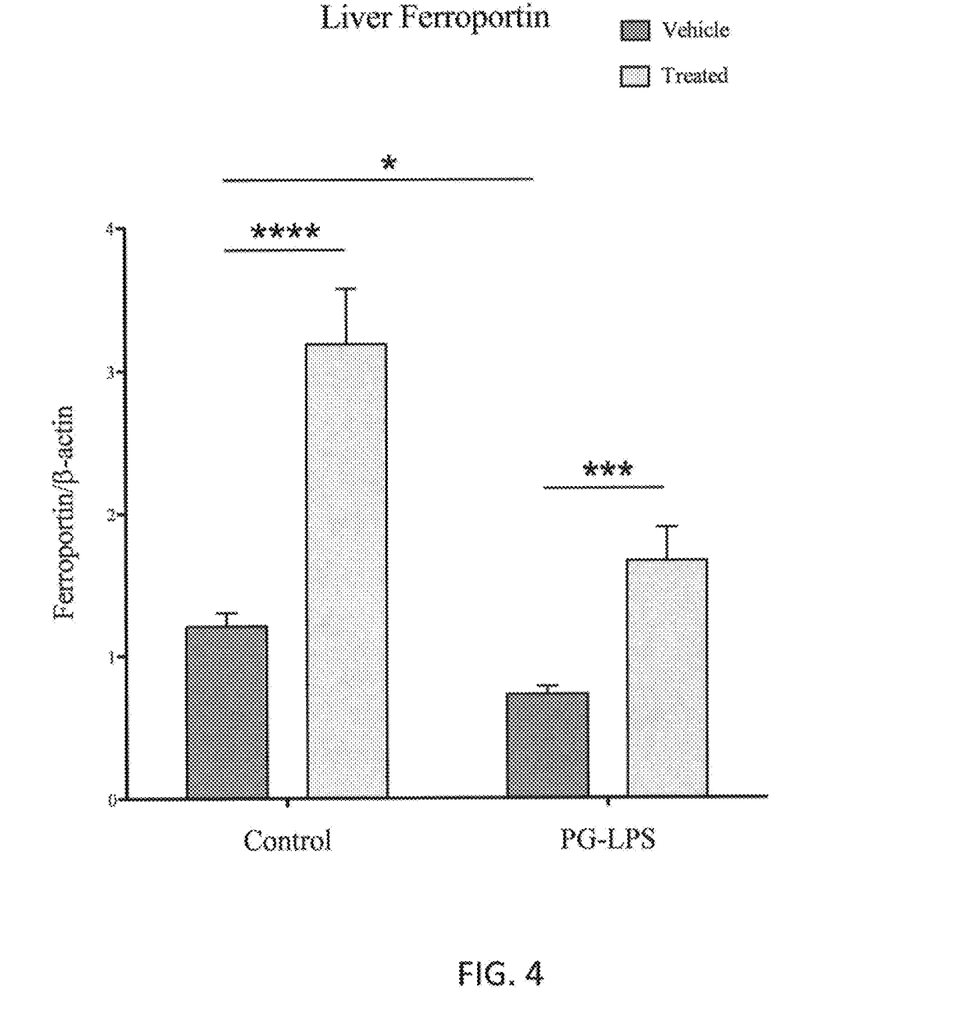
FIG. 4 shows ferroportin stabilization. Control, ferroportin on liver cells of healthy rats or rats treated with hepcidin inhibitors. PG-LPS rats were inflamed but drug treatment blocked hepcidin and increased ferroportin on the surface of liver cells. Rats treated with hepcidin inhibitors show more ferroportin on liver cells than untreated rats.
Figure 5:
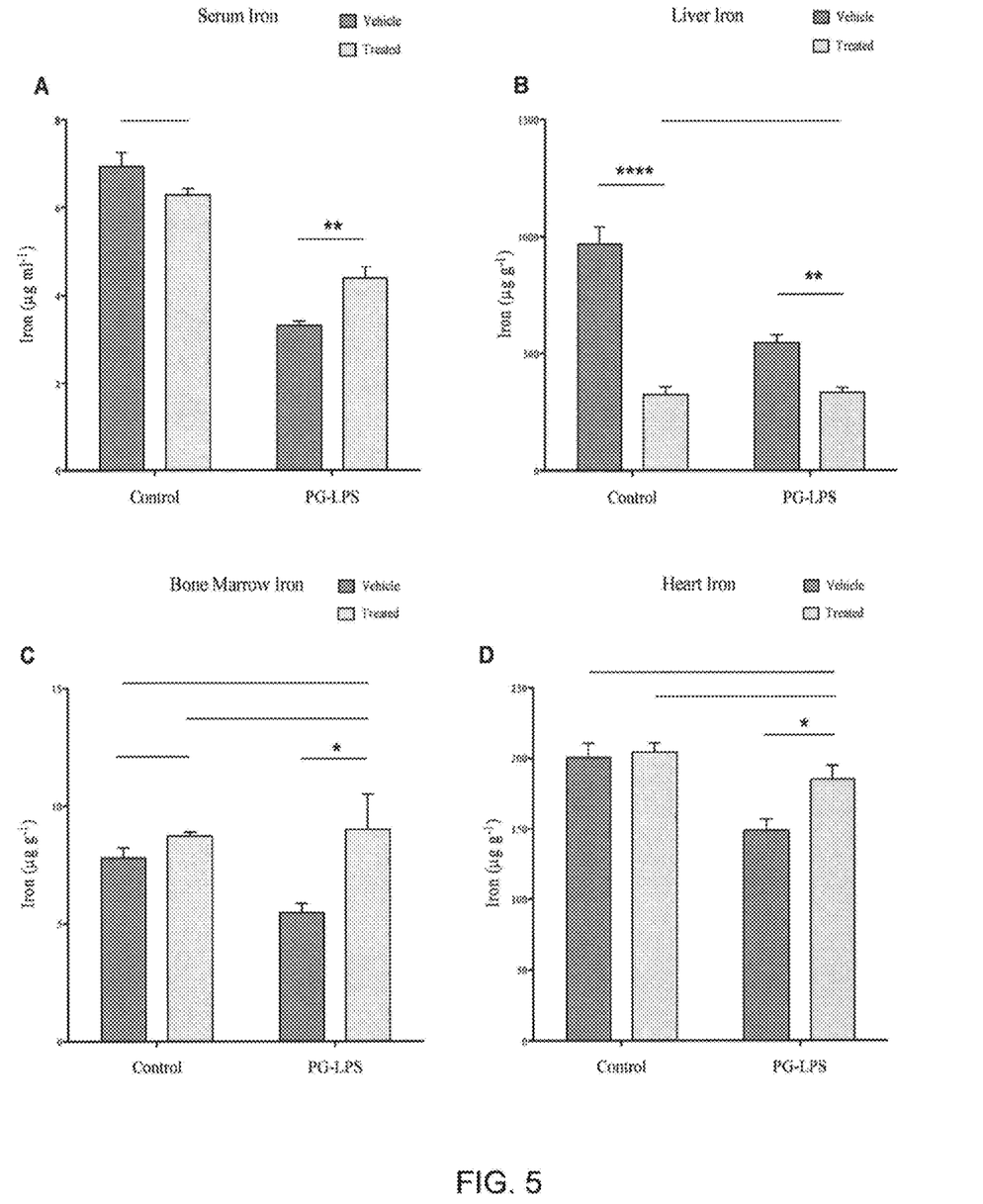
FIG. 5 shows iron concentration in serum and various tissues. (A) Serum iron decreases with Inflammation but increases when hepcidin inhibitors are added. B) Liver iron decreases with hepcidin inhibitors suggesting ferroportin can release iron to serum. C) Iron in bone marrow and D) heart decrease with inflammation. Hepcidin inhibitor treatment restores iron levels to both the C) bone marrow and D) the heart with inflammation.

Treatment with HIV protease inhibitors decreased hepcidin secretion from cells and in the serum of a rat model of inflammation (see FIGS. 4 and 5). The lower hepcidin levels stabilized ferroportin and increased serum iron levels and bone marrow iron levels. The liver and spleen iron levels dropped 2-fold to 4-fold in the inflamed rats or non-inflamed control rats, respectively. The potent stabilization of ferroportin in the control rats that were not inflamed and the 4-fold decrease in liver iron suggests that this treatment can be used, even in the absence of elevated hepcidin to stabilize ferroportin and allow tissue iron release through ferroportin.

Example 3

Furin fluorescence assay evaluating the effectiveness of HIV protease inhibitors to inhibit furin and block the activation of hepcidin from prohepcidin. The dose response is shown for each drug at 55, 110 and 220 micromolar doses of the drugs.

An example is shown in FIG. 4 showing enhanced stabilization of ferroportin and in FIG. 5 (panel B) where liver iron is exported into the bloodstream. Similar data for the spleen has also been obtained. Depending on the individual, two additional combination treatments might be required. The first is to use an iron chelator in combination with the HIV protease inhibitor to bind the iron in serum once the iron exits ferroportin. The iron chelator complex can be secreted through the kidneys (see FIG. 6).

The stabilization of ferroportin to initiate iron export from the liver and spleen will help alleviate the iron overload in these tissues of the RES. Ferroportin stabilization, however, might also facilitate iron import from ferroportin found on intestinal enterocytes and increase iron absorption. The data from an animal study, which is a model of chronic inflammation, showed lower total iron in the rat even with elevated hepcidin (which was only measured on the liver and not the intestinal enterocytes). Also, the control rat that was not inflamed also showed extensive iron release from the liver in the absence of inflammation or elevated hepcidin (see FIG. 4). These data suggest that dietary iron might have been selectively inhibited but the conditions in a human patient with thalassemia might be very different. To adapt to this potential increase in iron absorption, thalassemia patients can be treated with dietary iron binding molecules to precipitate dietary iron and make it unavailable for iron absorption. Such combined treatments on a regular or periodic cycle will allow iron sequestered in the RES to be released and enhance the health of the liver and spleen in thalassemia patients that require blood transfusions or have increased dietary iron absorption.

Figure 6:
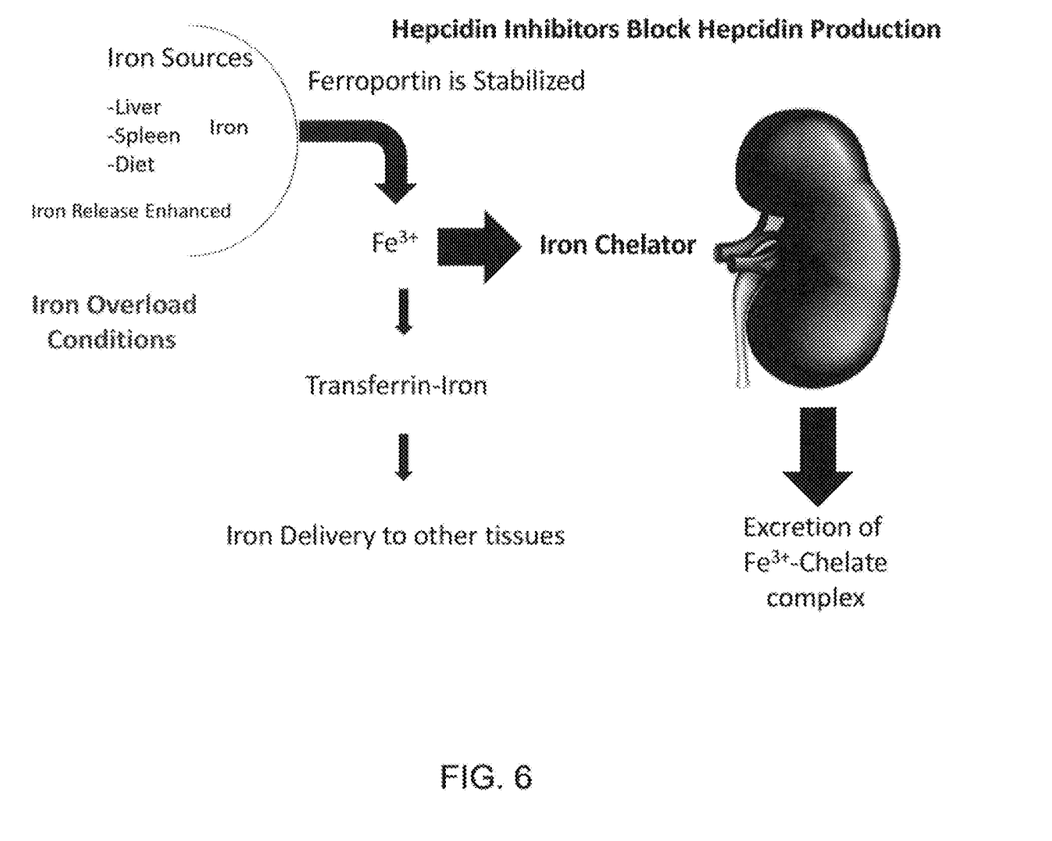
FIG. 6 shows a conceptual diagram of the suggested mechanism for treating iron overload using HIV protease inhibitors and an iron chelator. HIV protease inhibitors will prevent hepcidin formation and increase the stability of ferroportin in the cells of the liver and spleen. This will enhance iron release from iron-overloaded organs. As iron is exported to serum, the presence of iron chelators will compete with apo-transferrin to bind iron. The Chelator-$Fe^{3+}$ complex will be directed to the kidneys for excretion.

These data show that control animals that were not inflamed but were treated with the drugs Nelfinavir (catalytic site inhibitor) and Ritonavir (or Darunavir—which are both allosteric site inhibitors), showed a 3-fold increase in liver ferroportin (see FIG. 3) and a ~4-fold decrease in liver iron (see FIG. 5, panel B). In evaluating this observation, it was realized that this might be a pathway where tissue iron might be released in patients with hemochromatosis. In iron overload conditions, total iron levels are significantly elevated, and iron continues to be delivered to the organs by transferrin. However, if iron release from tissues was enhanced by stabilized ferroportin and could be combined with a serum iron chelator such as, Desferal, deferasirox or deferiprone, the iron-chelator complex could be secreted. The problem with transferrin acquiring iron from the iron chelators could be overcome by using Desferal that possesses a higher affinity for iron than transferrin, minimizing the delivery of iron back to the organs. The rapid secretion of the other iron-chelate complexes, however, may be sufficiently rapid to excrete iron when it is actively exported into the blood stream by ferroportin. Additionally, the transfer of some iron back to transferrin by these chelators might minimize some of the side effects of the more powerful iron chelators depleting the serum iron levels. Ultimately, the excess iron in the form of an iron-chelator complex should be cleared by the kidneys resulting in lower total body iron. FIG. 6 represents a model for how HIV protease inhibitor treatments to stabilize ferroportin, in combination with iron chelators would be enacted.

Similar to the discussion with thalassemia, ferroportin stabilization could enhance iron uptake from the diet. An additional combination treatment would include oral iron binding treatments to the diet to precipitate dietary iron to minimize iron absorption from the diet.

Figure 7:
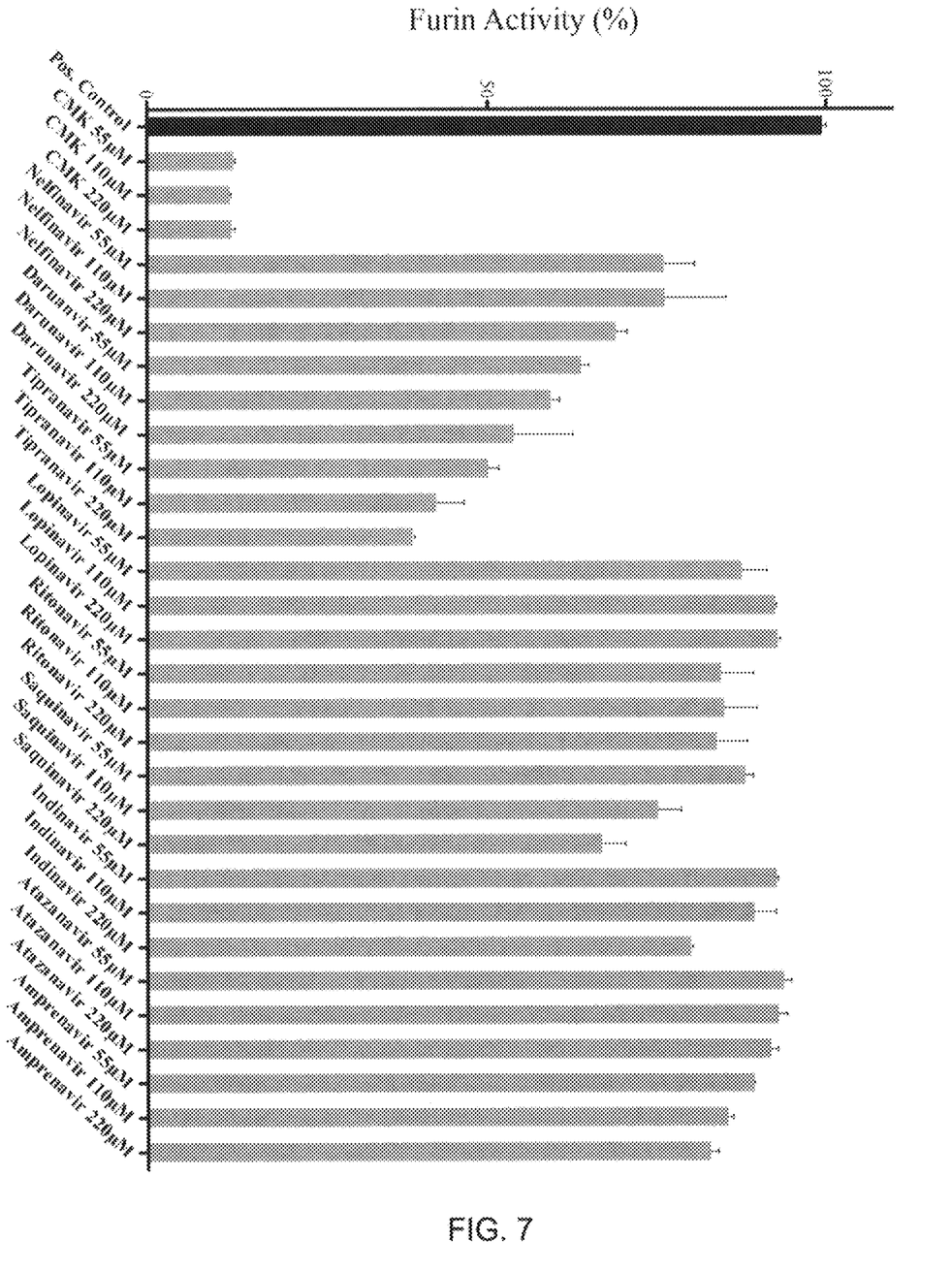
FIG. 7 shows furin activity as a function of various HIV protease inhibitors at various concentrations.

Experiment data suggested that nelfinavir and darunavir (or ritonavir) and also tipranavir possessed the most potent furin inhibition based on the in vitro fluorescence assay (see FIG. 7). Saquinavir and indinavir showed very weak dose dependent inhibition of furin.

Example 4

Figure 8:
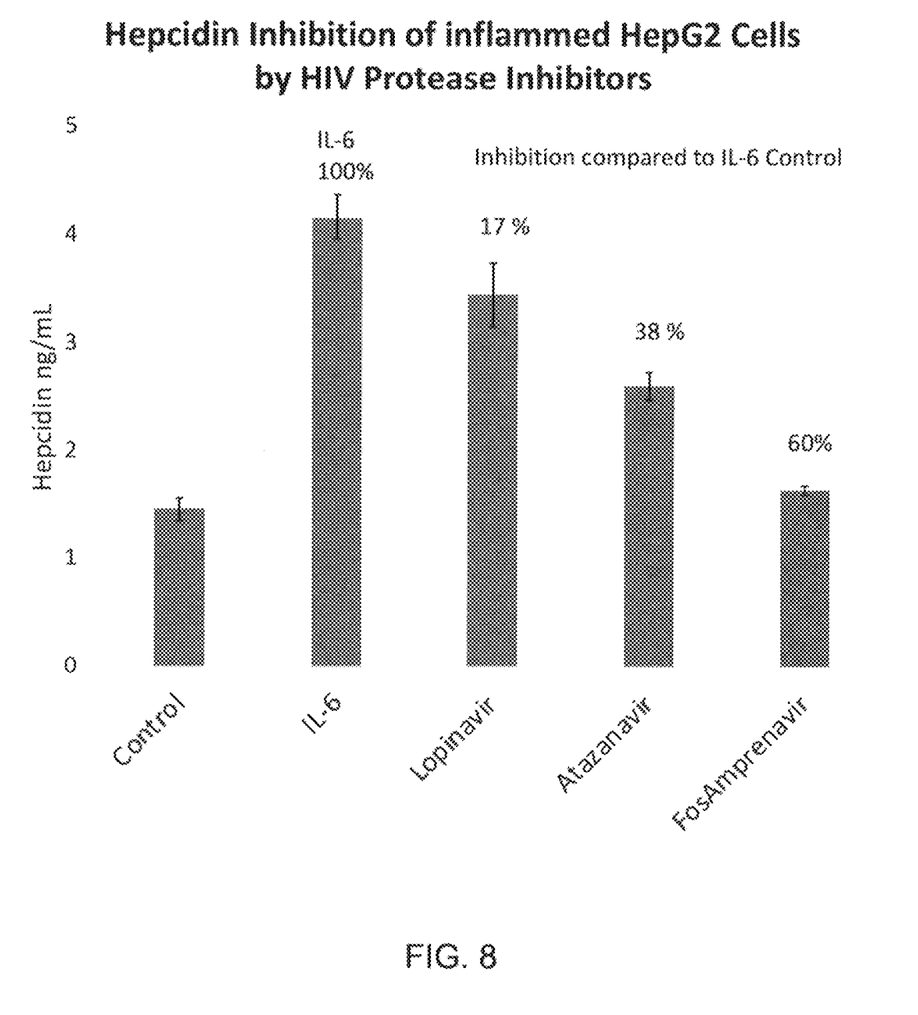
FIG. 8 shows that HIV protease inhibitors block hepcidin secretion from inflamed HepG2 cells.

HepG2 cells were cultured with controls not treated with additional treatments. The remaining cells were all treated to induce inflammation IL-6 (10 ng/mL). Inhibitors were added at 10 ng/mL to block furin and prevent the cleavage of prohepcidin to hepcidin. Hepcidin secreted into the growth media was measured by ELISA. Lopinavir, atazanavir and fosamprenavir (the prodrug of amprenavir) all showed inhibition of hepcidin secretion (see FIG. 8).

Figure 9:
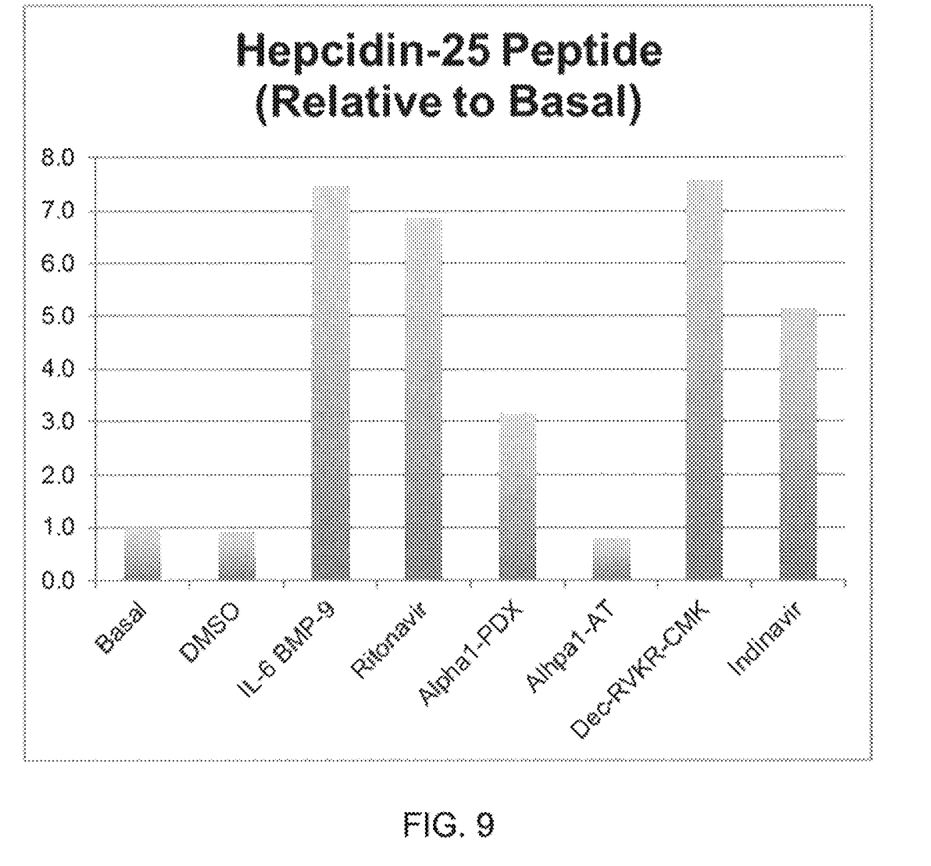
FIG. 9 shows inhibition of hepcidin secretion from HepG2 cells by inhibiting furin.

HepG2 cells were cultured with controls not treated with additional treatments. The remaining cells were all treated to induce inflammation IL-6 and BMP-9 (both cytokines were dosed at 10 ng/mL). Inhibitors were added at 10 micromolar to block furin and prevent the cleavage of prohepcidin to hepcidin. Hepcidin secreted into the growth media was measured by Mass Spectrometry. Ritonavir showed a small inhibitory effect and indinavir showed a more potent response to inhibiting hepcidin secretion. Alphal-PDX and Alphal-AT are known furin inhibitors (see FIG. 9).

Although the invention herein has been described in connection with described embodiments thereof, it will be appreciated by those skilled in the art that additions, modifications, substitutions, and deletions not specifically described may be made without departing from the spirit and scope of the invention as defined in the appended claims. It is, therefore, intended that the foregoing detailed description be regarded as illustrative rather than limiting, and that it be understood that it is the following claims, including all equivalents, that are intended to define the spirit and scope of this invention.

What is claimed is:

1. A method of treating iron overload in a patient having β-thalassemia major, comprising administering to the patient a therapeutically effective amount of nelfinavir to inhibit hepcidin formation by inhibiting furin leading to iron release from iron overloaded organs deferiprone to remove serum iron.

2. The method of claim 1, further comprising administering to the patient a therapeutically effective amount of ritonavir.

3. The method of claim 1, wherein the patient is undergoing dialysis.

4. The method of claim 1, wherein the administration of the therapeutically effective amount of nelfinavir and deferiprone to the patient lowers serum hepcidin concentration.

5. The method of claim 1, wherein the administration of the therapeutically effective amount of nelfinavir and deferiprone to the patient lowers iron concentration in reticuloendothelial system.

6. The method of claim 5, wherein the patient is diagnosed with myelofibrosis.

7. The method of claim 1, wherein iron concentration in the spleen is reduced.

8. The method of claim 1, wherein nelfinavir and deferiprone are provided as a pharmaceutical composition for oral administration.

9. The method of claim 2, wherein nelfinavir, ritonavir, and deferiprone are provided as a pharmaceutical composition for oral administration.

10. The method of claim 1, wherein the nelfinavir is administered at a dose of about 750 mg daily for adults.

11. The method of claim 1, further comprising measuring a patient's serum hepcidin concentration.

* * * * *